United States Patent
Ura

(10) Patent No.: US 10,085,692 B2
(45) Date of Patent: Oct. 2, 2018

(54) EXERCISE SUPPORT DEVICE, EXERCISE SUPPORT METHOD, AND COMPUTER-READABLE STORAGE MEDIUM HAVING EXERCISE SUPPORT PROGRAM STORED THEREIN

(71) Applicant: CASIO COMPUTER CO., LTD., Shibuya-ku, Tokyo (JP)

(72) Inventor: Kazuo Ura, Fussa (JP)

(73) Assignee: CASIO COMPUTER CO., LTD., Tokyo (JP)

(*) Notice: Subject to any disclaimer, the term of this patent is extended or adjusted under 35 U.S.C. 154(b) by 808 days.

(21) Appl. No.: 14/106,385

(22) Filed: Dec. 13, 2013

(65) Prior Publication Data

US 2014/0172136 A1 Jun. 19, 2014

(30) Foreign Application Priority Data

Dec. 18, 2012 (JP) .................. 2012-275946

(51) Int. Cl.
*A63F 13/00* (2014.01)
*A61B 5/00* (2006.01)
*A61B 5/11* (2006.01)

(52) U.S. Cl.
CPC ............... *A61B 5/681* (2013.01); *A61B 5/11* (2013.01); *A61B 5/1112* (2013.01)

(58) Field of Classification Search
CPC .................................................... A61B 5/681
See application file for complete search history.

(56) References Cited

U.S. PATENT DOCUMENTS

| | | |
|---|---|---|
| 6,837,827 B1 | 1/2005 | Lee et al. |
| 7,566,290 B2 | 7/2009 | Lee et al. |
| 7,601,098 B1 | 10/2009 | Lee et al. |
| 7,662,064 B2 | 2/2010 | Lee et al. |

(Continued)

FOREIGN PATENT DOCUMENTS

| | | |
|---|---|---|
| JP | 10-039059 A | 2/1998 |
| JP | 2002346013 A | 12/2002 |

(Continued)

OTHER PUBLICATIONS

Japanese Office Action dated Feb. 3, 2015, issued in counterpart Japanese Application No. 2012-275946.

(Continued)

*Primary Examiner* — Kang Hu
*Assistant Examiner* — Thomas H Henry
(74) *Attorney, Agent, or Firm* — Holtz, Holtz & Volek PC

(57) ABSTRACT

An exercise support device includes: a display section which has a display area where a first object as a virtual mobile object and a second object corresponding to a user are displayed; and a control section which controls display positions of the first object and the second object in the display area. The control section, while the user is moving from a first point to a second point, controls such that the display position of the first object is set to a position corresponding to a first movement distance based on a set target pace and an elapsed time after the user starts movement; and that the display position of the second object is set to a position corresponding to a second movement distance that the user moves from the first point in the elapsed time.

19 Claims, 9 Drawing Sheets

(56) References Cited

U.S. PATENT DOCUMENTS

| | | | |
|---|---|---|---|
| 7,789,802 B2 | 9/2010 | Lee et al. | |
| 8,107,679 B2 * | 1/2012 | Yoda | G06K 9/00369 382/103 |
| 2005/0288154 A1 | 12/2005 | Lee et al. | |
| 2007/0149362 A1 * | 6/2007 | Lee | A63B 24/0021 482/8 |
| 2012/0166257 A1 * | 6/2012 | Shiragami | G06Q 30/0207 705/14.1 |
| 2014/0172136 A1 | 6/2014 | Ura | |

FOREIGN PATENT DOCUMENTS

| | | |
|---|---|---|
| JP | 2004016738 A | 1/2004 |
| JP | 2014117512 A | 6/2014 |

OTHER PUBLICATIONS

Japanese Office Action (and English translation thereof) dated Sep. 29, 2015, issued in counterpart Japanese Application No. 2012-275946.

Japanese Office Action dated May 3, 2018, issued in counterpart Japanese Application No. 2017-038970.

\* cited by examiner

FIG. 1A
FIG. 1B
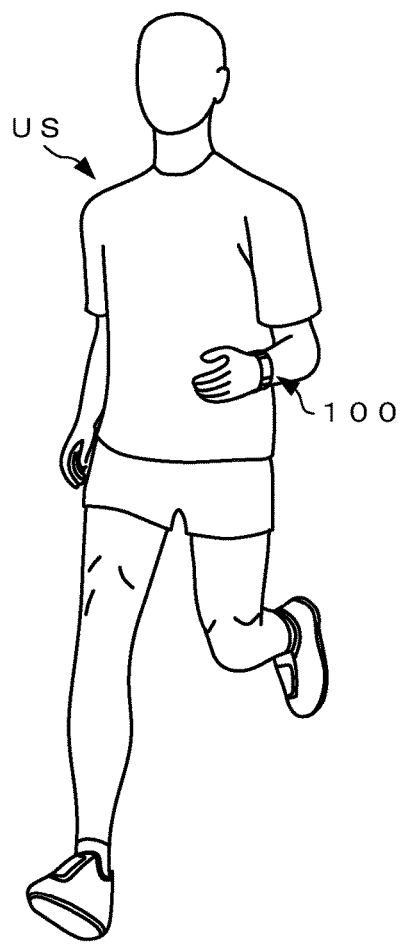
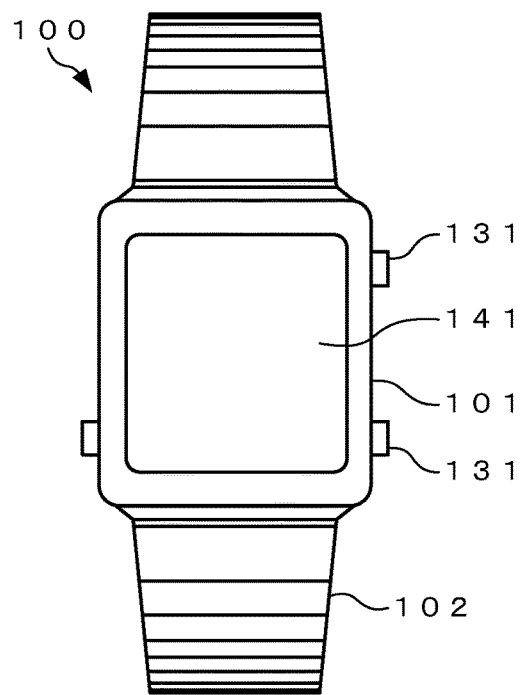

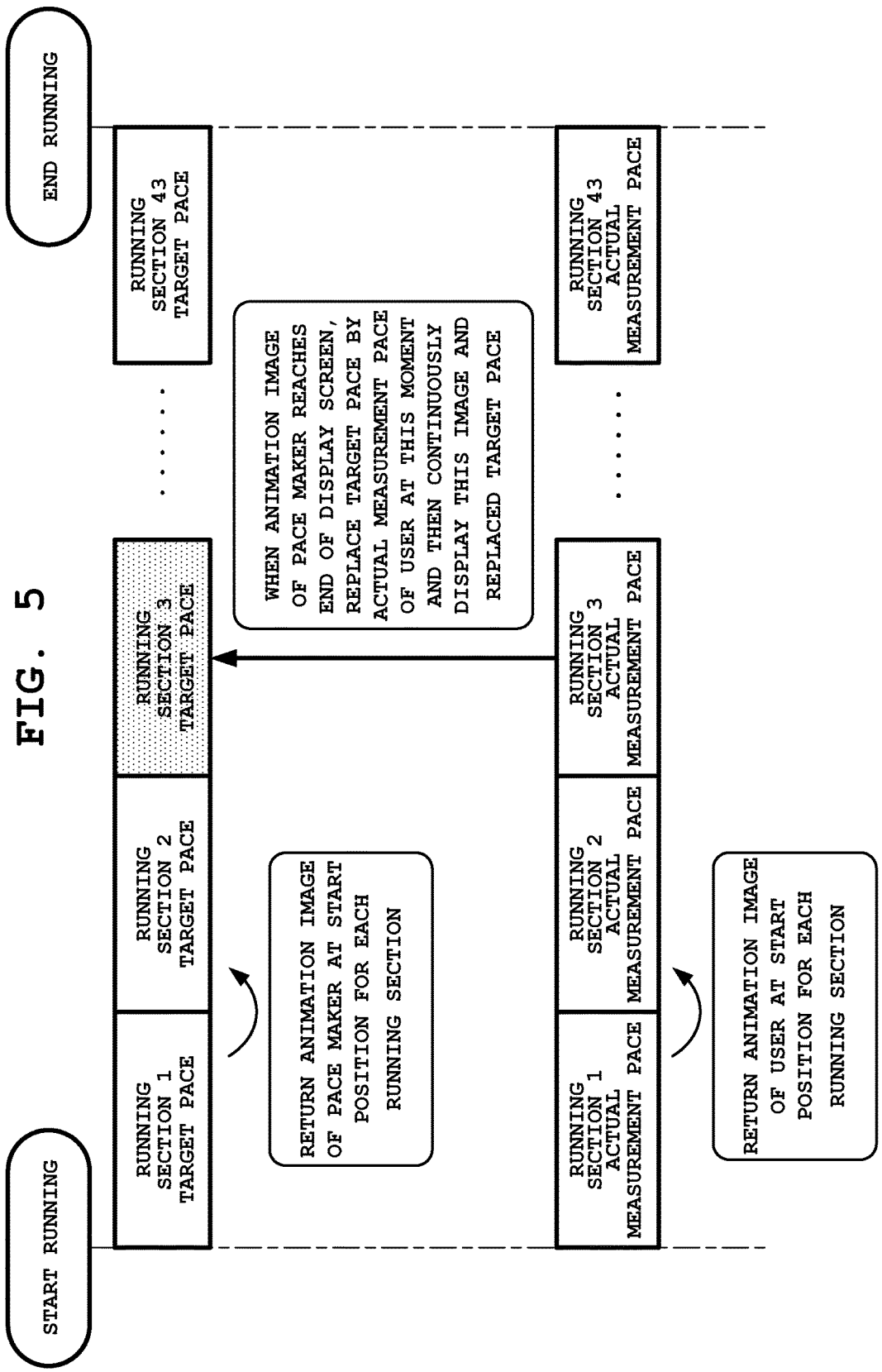

EXERCISE SUPPORT DEVICE, EXERCISE SUPPORT METHOD, AND COMPUTER-READABLE STORAGE MEDIUM HAVING EXERCISE SUPPORT PROGRAM STORED THEREIN

CROSS-REFERENCE TO RELATED APPLICATION

This application is based upon and claims the benefit of priority from the prior Japanese Patent Application No. 2012-275946, filed Dec. 18, 2012, the entire contents of which are incorporated herein by reference.

BACKGROUND OF THE INVENTION

1. Field of the Invention

The present invention relates to an exercise support device, exercise support method, and computer-readable storage medium having an exercise support program stored therein and, in particular, to an exercise support device, exercise support method, and computer-readable storage medium having an exercise support program stored therein including a pace making function for guiding an exercise motion such as running or walking to a desired pace.

2. Description of the Related Art

In recent years, because of rising health consciousness, more and more people are performing daily exercises, such as running, walking, and cycling, to maintain their wellness or improve their health condition.

In addition, an increasing number of people are aiming to participate in competitions, such as marathon events and cycling races, through these daily exercises.

Among these people aiming to participate in competitions, there is a rising demand for efficient and effective training methods that enable them to achieve good results in the competitions. Currently, various products and technologies are being developed for meeting such a demand.

For example, Japanese Patent Application Laid-Open (Kokai) Publication No. 10-039059 describes a stopwatch with a built-in GPS (Global Positioning System). In the stopwatch, positioning data including time, position, speed, etc. is calculated by a GPS receiver from a signal received from a GPS satellite. Based on the positioning data, measurement data including running data such as running time, running distance, and average speed is calculated. Then the measurement data is displayed on a display device and provided to a runner (user).

In the technology described in Japanese Patent Application Laid-Open (Kokai) Publication No. 10-039059, various measurement data including running data of the user (such as running distance, average speed, lap time, and goal time) are automatically calculated based on the positioning data obtained from the GPS, and are provided to the running user via the display device.

Here, in a stopwatch-type or wristwatch-type device to be mounted on the human body, various information is generally displayed on the display device in a form of numerical values, and is provided to the user.

However, it is difficult to instantaneously and accurately read the displayed numerical values, since the user cannot stare at the display screen of the device during exercise. In addition, it is difficult to instantaneously grasp the meaning of the display content unless the user sufficiently understands the meaning of the display numerical values.

Moreover, in the technology described in Japanese Patent Application Laid-Open (Kokai) Publication No. 10-039059, various running information is merely calculated based on the positioning data of the user during running and provided to the user.

That is, it is not possible to achieve a so-called pace making function of guiding the running of the user when training is performed for achieving a desired record in running or the like.

SUMMARY OF THE INVENTION

The present invention has an advantage of providing an exercise support device, exercise support method, and computer-readable storage medium having an exercise support program stored therein capable of achieving a pace making function of guiding an exercise motion of a user to a desired pace and also capable of making the user intuitively grasp a status during the exercise.

In accordance with one aspect of the present invention, there is provided an exercise support device comprising: a display section which has a display area where a first object as a virtual mobile object and a second object corresponding to a user are displayed; and a control section which controls display positions of the first object and the second object in the display area, wherein the control section, while the user is moving from a first point to a second point, controls such that: the display position of the first object is set to a position corresponding to a first movement distance based on a set target pace and an elapsed time after the user starts movement, and the display position of the second object is set to a position corresponding to a second movement distance that the user moves from the first point in the elapsed time.

In accordance with another aspect of the present invention, there is provided an exercise support method comprising: a step of displaying a first object as a virtual mobile object and a second object corresponding to a user in a display area of a display section; a step of controlling, while the user is moving from a first point to a second point, such that a display position of the first object is set to a position corresponding to a first movement distance based on a set target pace and an elapsed time after the user starts movement, and that the first object moves according to a progress of the elapsed time; and a step of controlling, while the user is moving from the first point to the second point, such that a display position of the second object is set to a position corresponding to a second movement distance that the user moves from the first point in the elapsed time, and that the second object moves according to movement of the user.

In accordance with another aspect of the present invention, there is provided a non-transitory computer-readable storage medium having stored thereon a program that is executable by a computer, the program being executable by the computer to perform functions comprising: processing for displaying a first object as a virtual mobile object and a second object corresponding to a user in a display area of a display section; processing for controlling, while the user is moving from a first point to a second point, such that a display position of the first object is set to a position corresponding to a first movement distance based a set target pace and an elapsed time after the user starts movement, and that the first object is displayed in a manner to move according to a progress of the elapsed time; and processing for controlling, while the user is moving from the first point to the second point, such that is set a display position of the second object to a position corresponding to a second movement distance when the user moves from the first point in the elapsed time, and that the second object is displayed in a manner to more according to the movement of the user.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

BRIEF DESCRIPTION OF THE DRAWINGS

FIG. 1A and FIG. 1B are schematic structural diagrams of a first embodiment of the exercise support device according to the present invention;

FIG. 5 is a conceptual diagram of an example of settings of a target pace in the exercise support method according to the first embodiment;

DETAILED DESCRIPTION OF THE PREFERRED EMBODIMENTS

The exercise support device, exercise support method, and exercise support program according to the present invention will be described in detail below by presenting embodiments.

In the description below, an exercise support device for achieving a pace making function when the user of the exercise support device according to the present invention performs running will be described, <First Embodiment>

(Exercise Support Device)

FIG. 1A and FIG. 1B are schematic structural diagrams of a first embodiment of the exercise support device according to the present invention.

Figure 2:
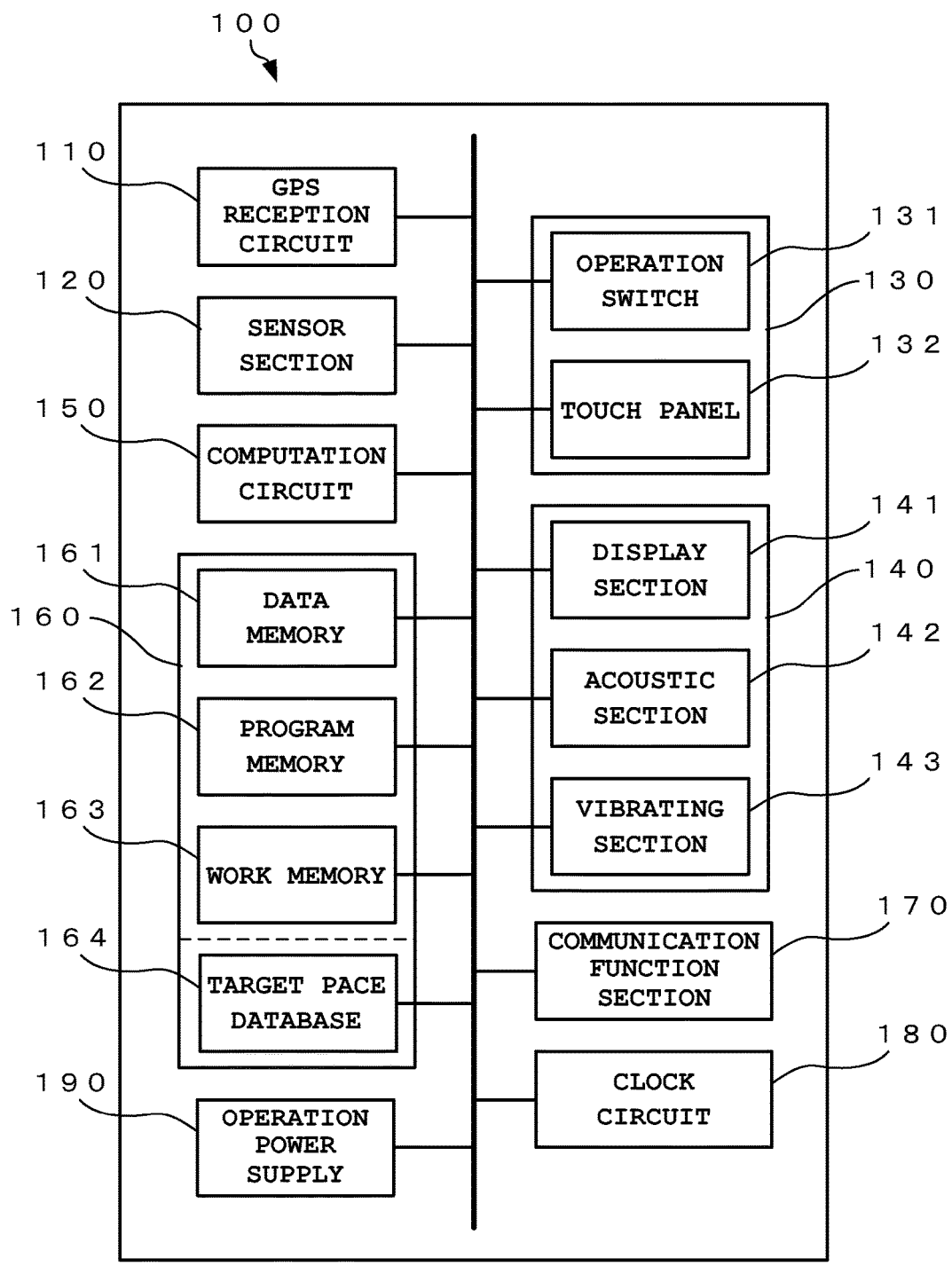
FIG. 2 is a block diagram of main sections of an example of control configuration of a wrist mounted type sensor device (a wrist device) applied to the exercise support device according to the first embodiment.

FIG. 2 is a block diagram of main sections of an example of control configuration of a wrist mounted type sensor device (a wrist device) applied to the exercise support device according to the present embodiment.

The exercise support device according to the first embodiment broadly has a wristwatch-type or wristband-type sensor device (hereinafter, referred to as a "wrist device" for convenience) 100 to be mounted on the wrist of a user US as a device user, as depicted in FIG. 1A.

The wrist device 100 has an outer appearance structure broadly including a device body 101 which detects exercise information such as the position and moving speed of a user US and provides exercise support information for guiding the running of the user US (pace making); and a band section 102 which is wound around the wrist of the user US, whereby the device body 101 is mounted on the wrist.

Specifically, the wrist device 100 broadly includes a GPS reception circuit 110, a sensor section 120, an input interface section 130, an output interface section 140, a computation circuit 150, a memory section 160, a communication function section 170, a clock circuit 180, and an operation power supply 190, as depicted in FIG. 2, for example.

The GPS reception circuit 110 receives radio waves from a plurality of GPS satellites via a GPS antenna (omitted in the drawing), and thereby detects and outputs a geographic position based on latitude and longitude information as position data.

The GPS reception circuit 110 uses, for example, a Doppler shift effect of radio waves from the GPS satellites, and thereby detect and output a movement speed of the user US as speed data.

The speed data may be a movement speed calculated by the computation circuit 150, which will be described further below, based on the above-described position data and an elapsed time.

GPS data (sensor data) including the above-described position data and speed data is associated with time data regulated by the clock circuit 180, which will be described further below, and stored in a predetermined storage area of a data storage memory 161 of the memory section 160.

The GPS reception circuit 110 may obtain not only the position data based on the latitude and longitude information but also time data. In this case, the time data is used for time display on a display section 141 of the output interface section 140, which will be described further below, time data correction regulated by the clock circuit 180, and other purposes.

The sensor section 120 has a geomagnetic sensor (an electronic compass), for example. The sensor section 120 detects the magnetic field of the earth and thereby outputs direction data indicating a travelling direction (a moving direction) of the user US.

Here, the direction data obtained by the geomagnetic sensor is used to complement the GPS data obtained by the GPS reception circuit 110 and improve accuracy of the GPS data.

As with the GPS data, the direction data obtained by the sensor section 120 is associated with the time data regulated by the clock circuit 180 and is stored in a predetermined storage area of the data storage memory 161 of the memory section 160.

In the exercise support device according to the present embodiment, when the position data and the speed data obtained by the GPS reception circuit 110 have sufficient accuracy, the exercise support device may have configuration without the geomagnetic sensor.

The sensor section 120 may further have an acceleration sensor or an angular velocity sensor (a gyro sensor) to detect the movement of the human body such as arm swing or exercise rhythm.

By these sensors of the sensor section 120, the acceleration and angular velocity of the user US during exercise are detected and outputted as acceleration data and angular velocity data. As with the direction data, the acceleration data and angular velocity data are associated with time data and are then stored in the data storage memory 161.

The input interface section 130 has an operation switch 131 and a touch panel 132, as depicted in FIG. 2, for example.

The operation switch 131 is a push-button-type switch provided in a manner to project on a side surface of the device body 101, as depicted in FIG. 1B, for example. This operation switch 131 is used for ON/OFF control of sensing operations of the GPS reception circuit 110 and the sensor section 120 and various input operations such as inputting and setting a target pace, which will be described further below, and setting an item to be displayed on the display section 141 of the output interface section 140.

The touch panel 132 is arranged on a front surface side (a side to be viewed) of the display section 141 provided to the output interface section 140, which will be described further below, or is integrally formed on the front surface side of the display section 141. By that a touch operation is performed on an area of the touch panel 132 corresponding to information displayed on the display section 141, a function corresponding to the information is selectively performed.

Here, the function achieved by the touch panel 132 may be equivalent to a function achieved by the operation switch 131 or a function unique to an input operation via the touch panel 132.

The input interface section 130 may be configured, for example, to include either one of the operation switch 131 and the touch panel 132.

The output interface section 140 has the display section 141, an acoustic section 142, and a vibrating section 143, as depicted in FIG. 2, for example.

The display section 141 has a display panel of, for example, a liquid-crystal type capable of color or monochrome display or a light-emitting-element type such as an organic EL element.

The display section 141 causes at least the GPS data obtained by the GPS reception circuit 110, a setting screen for setting a target pace or the like in an exercise support method, which will be described further below, and exercise support information provided to guide the running of the user US to be displayed on the display panel.

The acoustic section 142 has an acoustic device such as a buzzer or loudspeaker. The acoustic section 142 generates sound information such as a predetermined timbre or sound pattern or a voice message to acoustically provide or report various information to the user US.

The vibrating section 143 has a vibrating device such as a vibration motor or a vibrator. The vibrating section 143 generates vibration information such as a predetermined vibration pattern and its intensity to tactually provide or report various information to the user US.

Here, various information provided or reported by the acoustic section 142 and the vibrating section 143 may be synchronized with information displayed on the display section 141.

The output interface section 140 may include at least the display section 141.

The memory section 160 broadly has the data storage memory (hereinafter abbreviated as a "data memory") 161, a program storage memory (hereinafter abbreviated as a "program memory") 162, a work data storage memory (hereinafter abbreviated as a "work memory") 163, and a target pace database 164, as depicted in FIG. 2, for example.

The data memory 161 has a non-volatile memory where the GPS data obtained by the GPS reception circuit 110 and the sensor section 120, and the target pace for use in the exercise support method, which will be described further below, etc., are each stored in a predetermined storage area.

The program memory 162 stores a control program for performing a predetermined operation at each configuration, such as a sensing operation at the GPS reception circuit 110 and the sensor section 120 and an operation of providing various information from the output interface section 140, and an algorithm program for performing a series of exercise support operations for guiding the running of the user US based on the target pace set in advance (the exercise support method) to cause predetermined exercise support information to be displayed on the display section 141 of the output interface section 140.

The work memory 163 temporarily stores various data for use in executing the control program and the algorithm program, and various data generated.

The target pace database 164 stores a target pace for using in the exercise support method, which will be described further below, or various data for generating a target pace.

Here, the target pace is generated based on, for example, training data including the GPS data obtained in past running of the user.

The memory section 160 may be partially or entirely constituted of, for example, a removable storage medium such as a memory card, which can be detachably attached to the wrist device 100.

The computation circuit 150 is a computing device such as a CPU (Central Processing Unit) or a MPU (microprocessor). The computation circuit 150 executes a predetermined control program stored in the program memory 162, based on an operation clock generated by the clock circuit 180, which will be described further below.

As a result, the computation circuit 150 controls various operations such as the sensing operation at the GPS reception circuit 110 and the sensor section 120, and the information proving operation at the output interface section 140.

The computation circuit 150 executes a predetermined algorithm program stored in the program memory 162 based on the operation clock.

As a result, the computation circuit 150 performs a series of exercise support operations for guiding the running of the user US based on the target pace set in advance.

Note that the control program and the algorithm program to be executed by the computation circuit 150 may be incorporated in the computation circuit 150 in advance.

The communication function section 170 functions as an interface when various data are transmitted to and received from a device provided outside the wrist device 100 and the like.

Specifically, the communication function section 170 is used, for example, when the GPS data obtained during the running of the user US and other data are transferred to a storage section provided outside the wrist device 100 for backup storage and when the information to be displayed on the display section 141 is transmitted to an eyeglasses-type display device (a so-called head mount display) or the like for display.

Here, as a scheme of transmitting and receiving data between the wrist device 100 and the external device via the communication function section 170, any of various communication schemes such as WiFi (Wireless Fidelity: registered trademark) or Bluetooth (registered trademark) and wired communication schemes using a communication cable can be applied.

The clock circuit 180 has an oscillator which generates a base clock. Based on the base clock, the clock circuit 180 generates an operation clock that regulates operation timing of each component of the wrist device 100, time data indicating the current time, etc.

The time data such as the current time is displayed on the display section 141 of the output interface section 140, and provided to the user US.

The clock circuit 180 clocks timing of obtaining GPS data at the GPS reception circuit 110, timing of obtaining direction data at the sensor section 120, etc., and outputs it as time data.

The time data are associated with the obtained GPS data or the like and stored in the data memory 161.

The operation power supply 190 supplies driving electric power to each component inside the device body 101 of the wrist device 100.

As the operation power supply 190, for example, a primary battery such as a commercially-available coin-type battery or button-type battery or a secondary battery such as a lithium-ion battery or a nickel-metal-hydride battery can be applied. In addition a power supply by energy harvest technology for generating electricity by energy such as vibrations, light, heat, or electromagnetic waves may also be used as the operation power supply 190.

(Exercise Support Method)

Next, the exercise support method in the exercise support device according to the present embodiment is described.

Figure 3:
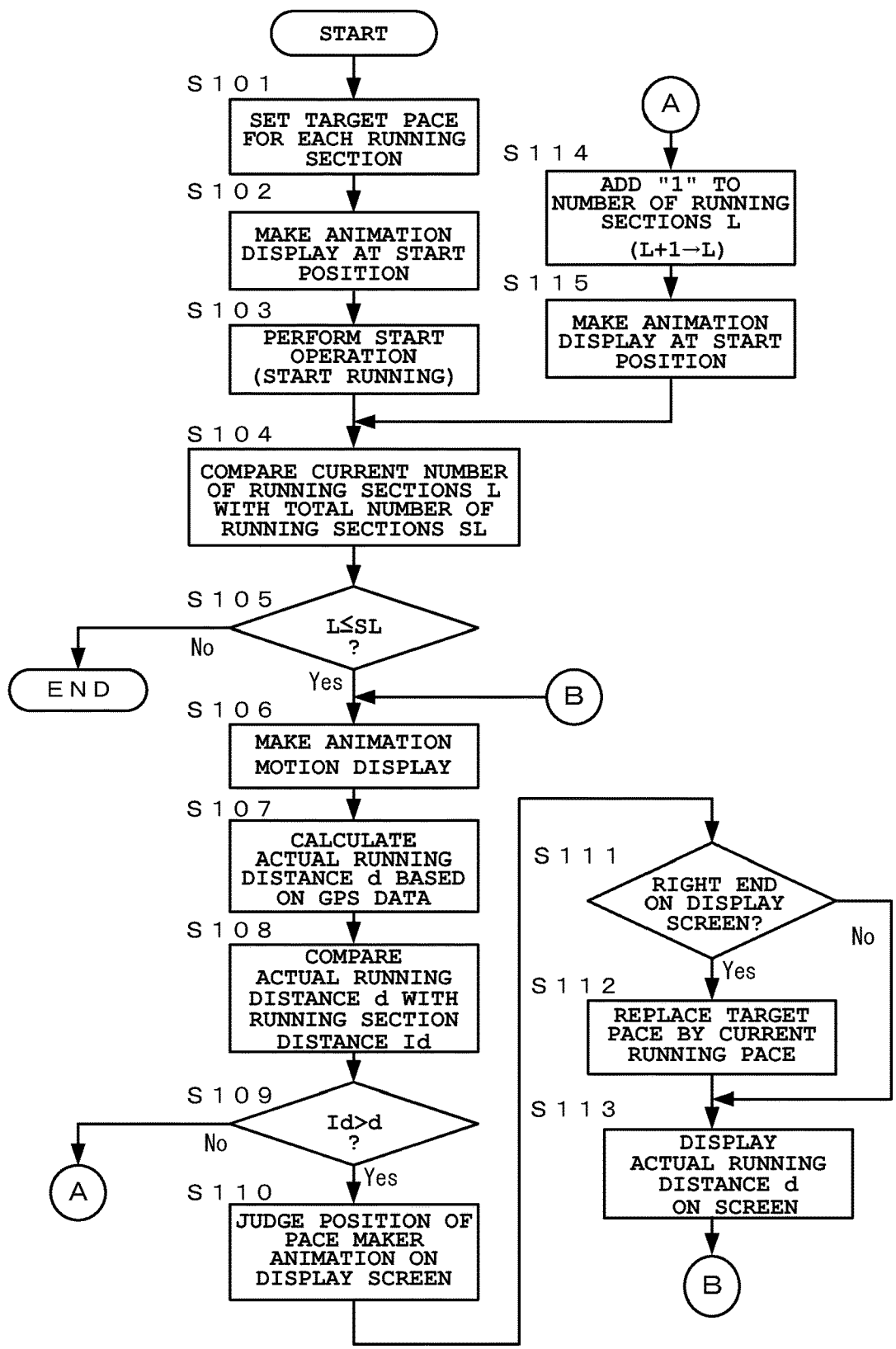
FIG. 3 is a flowchart of an example of the exercise support method in the exercise support device according to the first embodiment.

FIG. 3 is a flowchart of an example of the exercise support method in the exercise support device according to the present embodiment.

FIG. 4A, FIG. 4B, FIG. 4C, FIG. 4D and FIG. 4E are schematic views of screen display examples in the exercise support method according to the present embodiment.

FIG. 5 is a conceptual diagram of an example of settings of a target pace in the exercise support method according to the present embodiment.

In the exercise support method according to the present embodiment, as depicted in the flowchart of FIG. 3, for example, the user US first sets a target pace for the forthcoming running (Step S101).

Specifically, the user US operates the input interface section 130 of the wrist device 100, whereby the computation circuit 150 causes a target pace setting screen to be displayed on the display section 141 of the output interface section 140.

Next, the user US inputs an entire running distance of a course for the forthcoming running. As a result, the computation circuit 150 divides the running course for every predetermined section distance, and sets a plurality of running sections (or a lap sections).

For example, when the section distance is set at 1 km and running a distance equivalent to a full marathon (42.195 km) is performed, forty-three running sections are set in total, as depicted in FIG. 5.

For each of the running sections, the computation circuit 150 then extracts a target pace from the target pace database 164 of the memory section 160 based on training history of the user US. The computation circuit 150 then causes the extracted target paces to be stored in a predetermined storage area of the data memory 161 of the memory section 160 in association with the each of the running sections.

As a result, a target pace is set for each running section. The set target paces are set as running paces of a virtual mobile object (a virtual runner) as a pace maker.

Here, the target paces extracted from the target pace database 164 may be generated based on the running distance, and running time of the latest running, etc., from among the training data about past running performed by the user US.

Alternatively, when the target paces are stored in the target pace database 164 in association with geographic information (such as altitude and a course shape) of the running course and meteorological information (such as temperature, wind direction, and wind speed) as the training data, the target paces may be generated based on the running distance, running time, etc., which are extracted based on various conditions such as geographic information and meteorological information inputted by the user US.

The target paces may be generated by multiplying a running pace generated based on the training data of the user US stored in the target pace database 164 (that is, past running paces) by a predetermined coefficient in consideration of, for example, an exercise load, a degree of target achievement, etc.

Furthermore, the target paces are not limited to those generated based on the training data of the user US only, but may be, for example, those based on recordings of professional athletes or instructions from experts.

Still further, the target pace setting method is not limited to the scheme described above, in which a target pace generated based on the training data of the user US stored in the target pace database 164 is extracted and set for each running section.

The user US may directly operate the input interface section 130 to directly set a target pace with arbitrary numerical value for each running section.

Still further, the user US may directly operate the input interface section 130 to correct and set the target paces set by any of various schemes as described above.

Next, the computation circuit 150 causes an image as a pace maker and an image corresponding to the user US to be displayed on the display screen of the display section 141.

Figure 4A:
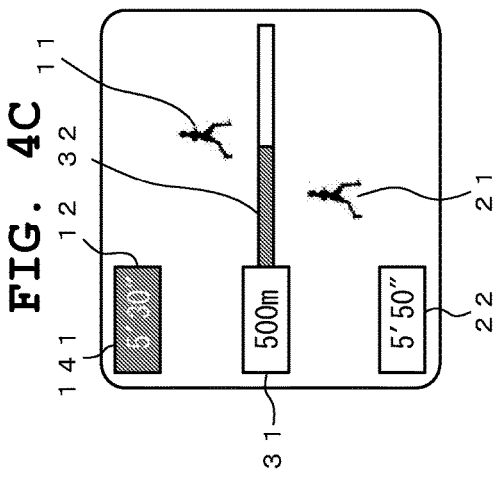
FIG. 4A, FIG. 4B, FIG. 4C, FIG. 4D and FIG. 4E are schematic views of screen display examples in the exercise support method according to the first embodiment.
Figure 4B:
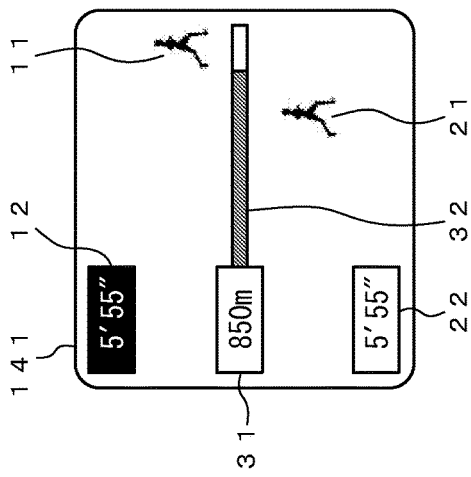

Here, as depicted in FIG. 4A and FIG. 4B, for example, a virtual object 11 as the image as a pace maker is displayed in an upper area on the display screen. An object 21 as the image corresponding to the user US is displayed in a lower area on the display screen. Here, the virtual object 11 and the object 21 are animation images which respectively have a human-like shape, for example, and move as if at least leg portions perform a running motion. The virtual object 11 and the object 21 may not be animation images but may be images which respectively have a human-like shape.

Before running starts or at the start of running, the virtual object 11 as a pace maker and the object 21 corresponding to the user US are displayed to be aligned at a start position (a starting point) set near the left end of the display screen, as depicted in FIG. 4B, for example (Step S102).

In the display screen of the display section 141 depicted in FIG. 4B, a target pace set at Step S101 is displayed above the virtual object 11 as a pace maker. As depicted in FIG. 4B, characters of the target pace of the virtual object 11 are displayed, for example, with white characters in a frame the inside of which is painted with black (a target pace display 12 in FIG. 4B). A display of "5' 30''" displayed herein indicates a running pace of five minutes and thirty seconds per kilometer.

In the display screen of the display section 141, an actual running pace (an actual measurement pace) of the user US is displayed below the object 21 corresponding to the user US. As depicted in FIG. 4B, characters of the running pace of the user US are displayed, for example, with black characters in a frame the inside of which is painted with white (an actual measurement pace display 22 in FIG. 4B). A display of "5' 40''" indicates a running pace of five minutes and forty seconds per kilometer.

As depicted in FIG. 4B, in an area between the virtual object 11 as a pace maker and the object 21 corresponding to the user US in a middle part of the display screen of the display section 141, a current running distance of the user US for each running section is displayed, for example, with black characters in a frame the inside of which is painted with white (an actual running distance display 31 in FIG. 4B), and an approximate position of the user US in each running section is displayed with a bar graph (a bar graph 32 in FIG. 4B).

Here, in the screen display examples depicted in FIG. 4B to FIG. 4E, a monochrome display panel is applied as the display section 141, and displays monochrome images, monochrome characters, monochrome graphics, etc. On the other hand, a color display panel may be applied to the display section 41. In this instance, images, characters and graphics, etc. may be displayed with arbitrary color.

Next, at the same time the user US starts running or before and after the start timing, the user US performs a start operation on the input interface section 130 (Step S103).

Next, the computation circuit 150 compares the cumulative number of running sections from the first running section where the user US starts running to the running section where the user US is currently running (the number of running sections) L with a total number of running sections SL set for the running course at Step S101 (Step S104).

Then, the computation circuit 150 judges whether the current number of running sections L is equal to or smaller than the total number of running sections SL, and thereby judges whether the user US has run the entire running distance of the running course. As a result, the computation circuit 150 determines whether to continue or end the processing of the exercise support method according to the present embodiment (Step S105).

When judging at Step S105 that the number of running sections L exceeds the total number of running sections SL (the judgment result of L≤SL is "No"), the computation circuit 150 judges that the user US has run the entire running distance of the running course. In this case, the computation circuit 150 ends the processing of the exercise support method according to the present embodiment (END).

On the other hand, when judging at Step S105 that the number of running sections L is equal to or smaller than the total number of running sections SL (the judgment result of L≤SL is "Yes"), the computation circuit 150 judges that the user US has not run the entire running distance of the running course yet. In this case, the computation circuit 150 performs the following exercise support operation based on the GPS data obtained by the GPS reception circuit 110.

Figure 4C:
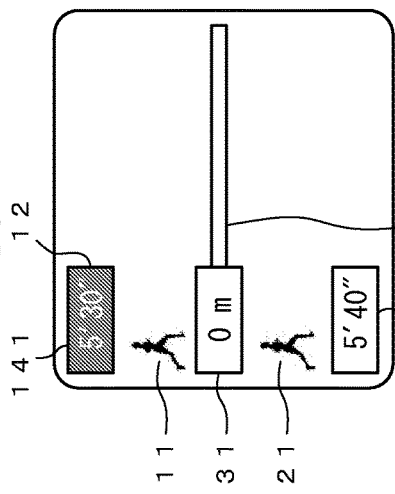

That is, the computation circuit 150 causes the virtual object 11 as a pace maker depicted in the upper part of the display screen to move rightward on the display screen at a speed according to the target pace set for the running section where the user US is currently running, as depicted in FIG. 4C, for example.

On the other hand, the computation circuit 150 causes the object 21 corresponding to the user US displayed in the lower part of the display screen to move rightward on the display screen at a speed according to the actual running pace (an actual measurement pace) of the user US based on the GPS data.

Here, while the user US is running, the computation circuit 150 causes the virtual object 11 as a pace maker and the object 21 corresponding to the user US to be displayed as animation images which respectively move as if a running motion is performed (Step S106).

Based on the GPS data, the computation circuit 150 calculates a distance (an actual running distance) d where the user US has actually run in the running section (Step S107).

Next, the computation circuit 150 compares the actual running distance d where the user has actually run with a distance of the running section set in advance (a running section distance) Id (Step S108).

The computation circuit 150 then judges whether the actual running distance d is shorter than the running section distance Id, and thereby judges whether the user US has completely run the running section. As a result, the computation circuit 150 determines whether to continue the display operation of the virtual object 11 and the object 21 corresponding to the user US in that running section, or whether to proceed to processing on the running section set next (Step S109).

When judging at Step S109 that the actual running distance d has reached the running section distance Id and the user US ends running of the running section (the judgment result of Id>d is "NO"), the computation circuit 150 adds (increments) "1" to the number of running sections and specifies the next running section (Step S114).

As with Step S102, the computation circuit 150 then returns the display position of the virtual object 11 as a pace maker and the object 21 corresponding to the user US to the start position on the display screen (Step S115).

Here, simultaneously, the computation circuit 150 displays a target pace set for the next running section in the target pace display 12 on the display screen, and resets the actual running distance display 31 to 0 m.

Next, the computation circuit 150 returns to Step S104 and performs the processing at Step S104 onward. That is, the computation circuit 150 compares the number of running sections L newly specified for the next running section with a total number of running sections SL, and thereby judges whether the user US has run the entire running distance of the running course.

On the other hand, when judging at Step S109 that the actual running distance d has not reached the running section distance Id and the user US has not ended running of the running section (the judgment result of Id>d is "Yes"), the computation circuit 150 judges, based on the target pace set for the running section, at which position on the display screen the virtual object 11 as a pace maker is displayed (Step S110).

Specifically, the computation circuit 150 calculates a movement distance as a pace maker based on the target pace and an elapsed time from the time when the user starts to run the running section, and compares the movement distance with the running section distance Id (for example, 1 km).

As a result, the computation circuit 150 judges the display position of the virtual object 11 on the display screen, and judges whether the display position has reached a right end of the display screen (that is, a position as an end point of the running section) (Step S111).

Figure 4D:
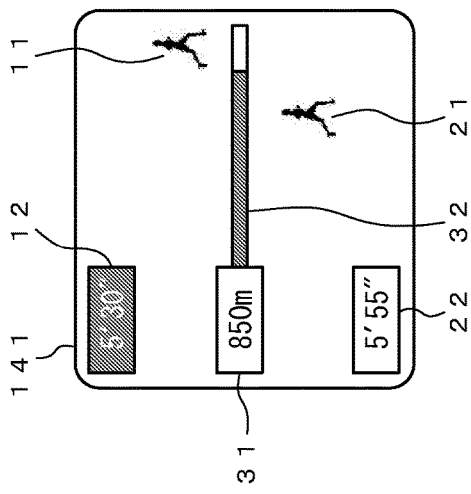
Figure 4E:
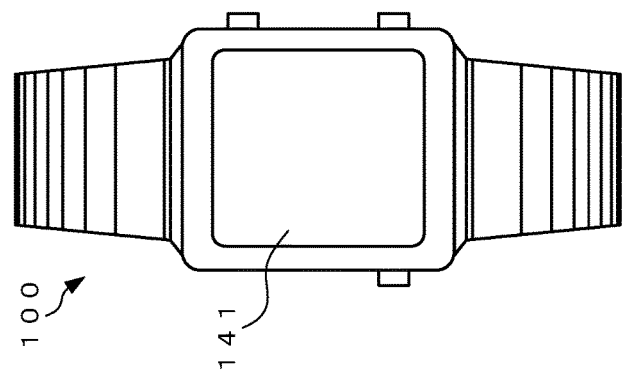

When judging at Step S111 that the virtual object 11 as a pace maker has reached the right end of the display screen (the judgment result of whether to reach the right end of the screen display is "Yes"), as depicted in FIG. 4D, the computation circuit 150 replaces the target pace set for the running section by the current running pace (actual measurement pace) of the user US calculated based on the GPS data, and displays the replaced target pace in the target pace display 12 on the display screen, as depicted in FIG. 45 (Step S112).

Next, the computation circuit 150 keeps the position of the virtual object 11 as a pace maker at the right end of the display screen, and causes the virtual object 11 as a pace maker to continue only the running motion (that is, causes the virtual object 11 as a pace maker to perform a stepping motion without going forward).

Here, the actual measurement pace at the time of the replacement is continuously (fixedly) displayed in the target pace display 12 until the user completely runs the running section.

Next, when judging after Step S112 or at Step S111 that the virtual object 11 as a pace maker has not reached the right end of the display screen (the judgment result of whether to reach the right end of the screen display is "No"), the computation circuit 150 causes the actual running distance d of the user US calculated at Step S107 to be displayed in the actual running distance display 31 arranged in the middle part of the display screen by using a numerical value.

The computation circuit 150 then causes the bar graph 32 having length corresponding to the actual running distance d to be displayed. This bar graph is displayed such that the length of the bar graph increases as the actual running distance d is increases.

Then, the computation circuit 150 again returns to the processing at Step S106 onward. That is, a the computation circuit 150 performs an operation of causing the virtual object 11 as a pace maker to be continuously displayed at the right end of the display screen or an operation of causing the virtual object 11 as a pace maker to move on the display screen according to the target pace set for the running section, and also performs an operation of causing the object 21 corresponding to the user US to move on the display screen at a speed according to the actual measurement pace.

The computation circuit 150 performs the series of processing as described above.

Then, when the user US ends running of the running section (that is, when the actual running distance d reaches the running section distance Id), the computation circuit 150 repeatedly performs similar processing on the next running section.

When the user US ends running of the running course set in advance (that is, when the number of running sections L exceeds the total number of running sections SL), the computation circuit 150 ends the processing of the exercise support method according to the present embodiment.

The series of processing described above is performed at arbitrary timing. This timing is set at, for example, one second or several seconds.

As such, in the exercise support method according to the present embodiment, as depicted in FIG. 5, arbitrary target pace is set for each running section of a running course inputted by the user US.

Then, even if the pace maker has ended running of the running section before the user US during running, the virtual object 11 as a pace maker is continued to be always displayed, and the actual measurement pace of the user US at the time when the pace maker has ended running of the running section is fixedly displayed (refer to a running section 3 in FIG. 5).

Furthermore, these virtual object 11 and the object 21 corresponding to the user US are returned to the predetermined start position every time the running section is updated (refer to running sections 1 and 2 in FIG. 5), and the target pace is sequentially updated.

If the user US has ended running of the running section before the pace maker during running, the computation circuit 150 judges that the actual running distance d has reached the running section distance Id, and proceeds to the next running section. Then, the computation circuit 150 causes the display positions of the virtual object 11 as a pace maker and the object 21 corresponding to the user US to be respectively returned to the start position on the display screen.

As such, in the present embodiment, in each running section, both of the virtual object 11 as a pace maker moving based on the target pace and the object 21 corresponding to the user US moving based on the actual measurement pace of the user US are always and simultaneously displayed on the display section 141 of the wrist device 100.

As a result, the user US cart view the display section 141 of the wrist device 100 mounted on the wrist during running, whereby the user US can instantaneously and intuitively compare and grasp the target pace and the actual measurement pace.

In the present embodiment, when the pace maker ends running of the running section before the user US, the actual measurement pace of the user US at the time when the pace maker has ended running of the running section is fixedly displayed. As a result, the user US can continue running as being always aware of trying to exceed the actual measurement pace.

Thus, according to the present embodiment, by comparing his or her own running pace with the target pace, the user US can conduct running as being always aware of the target pace or aware of trying to improve his or her own running pace, whereby appropriate pace making for achieving a desired record can be achieved.

In the present embodiment, the GPS data obtained during running by the above-described exercise support method and the geographic information, meteorological information, etc., of the running course are stored in the target pace database 164 as training data.

As a result, the training data in the target pace database 164 is sequentially updated. According to the latest various conditions of the running course, and the recent physical strength and running experiences of the user US, an optimum target pace can be generated and extracted, whereby more appropriate pace making can be achieved.

<Second Embodiment>

In the above-described first embodiment, the target pace database 164 for use in setting a target pace is incorporated in the wrist device 100.

In a second embodiment, a target pace database for use in setting a target pace is provided outside the wrist device 100.

Figure 6A:
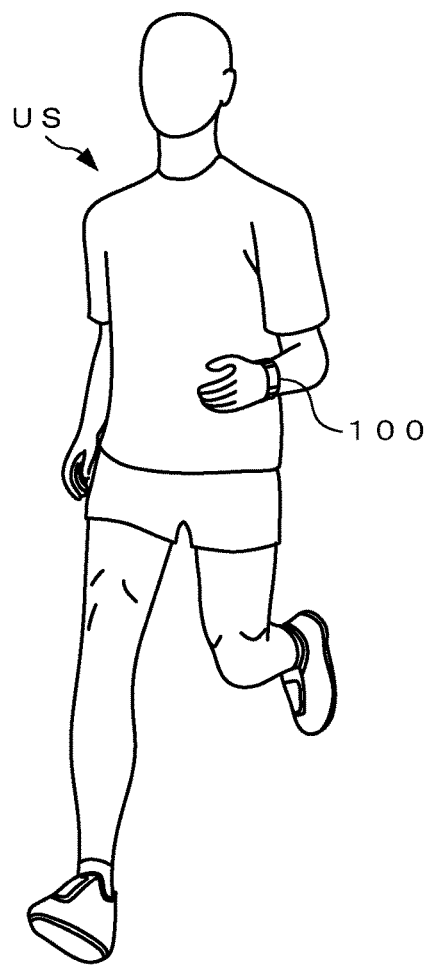
FIG. 6A and FIG. 6B are schematic structural diagrams of a first example of a second embodiment of the exercise support device according to the present invention.
Figure 6B:
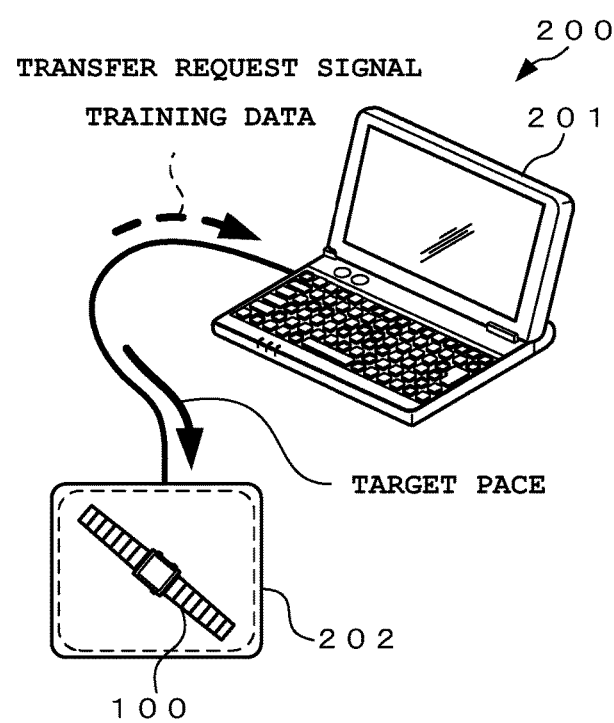

FIG. 6A and FIG. 6B are schematic structural diagrams of a first example of the second embodiment of the exercise support device according to the present invention.

Figure 7:
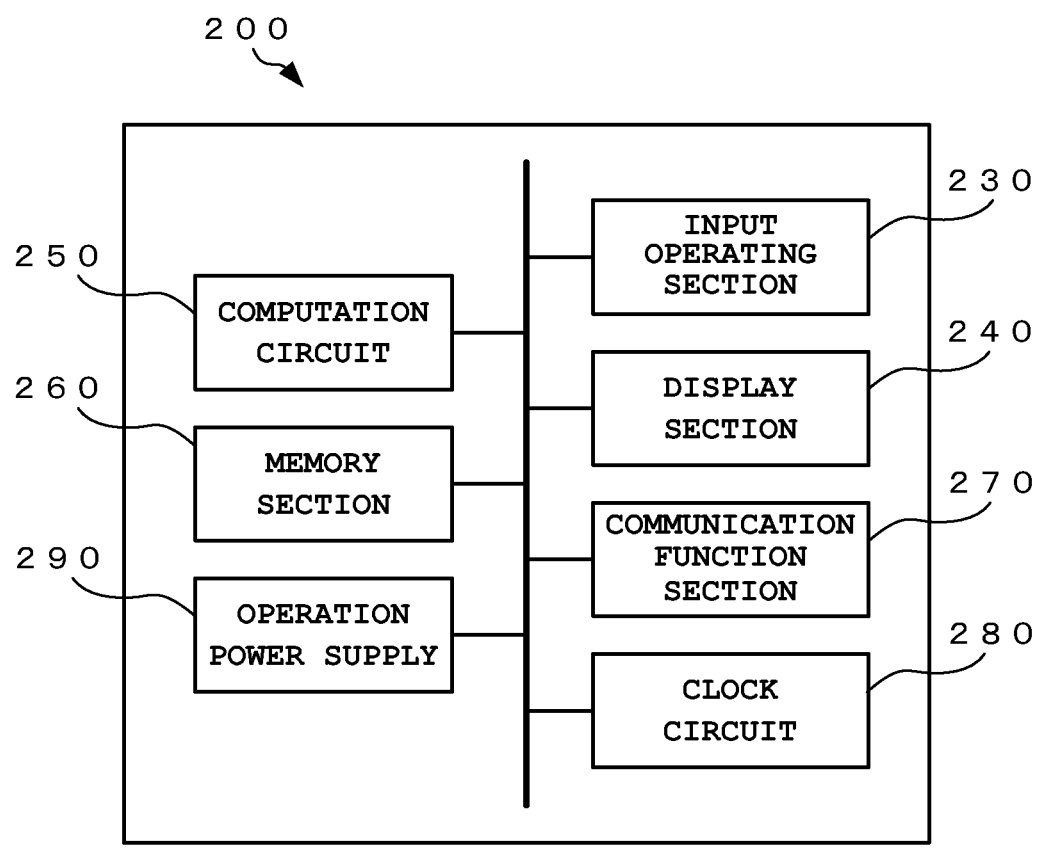
FIG. 7 is a block diagram of main sections depicting an example of control configuration of an information processing device applied to the exercise support device according to the second embodiment.

FIG. 7 is a block diagram of main sections depicting an example of control configuration of an information processing device applied to the exercise support device according to the present embodiment.

Here, components equivalent to those of the first embodiment are provided with the same reference numerals for simplification of description.

A first example of the exercise support device according to the second embodiment broadly has the wrist device 100 and an information processing device 200, as depicted in FIG. 6A and FIG. 6B, for example.

Here, the wrist device 100 has configuration in which the target pace database 164 is omitted (is not included) in the memory section 160 described in the first embodiment.

The information processing device 200 is a device capable of transmitting and receiving data to and from the wrist device 100. As depicted in FIG. 6B, for example, a laptop-type or desktop-type personal computer 201 can be applied as the information processing device 200.

Specifically, the information processing device 200 broadly includes an input operating section 230, a display section 240, a computation circuit 250, a memory section 260, a communication function section 270, a clock circuit 280, and an operation power supply 290, as depicted in FIG. 7, for example.

The input operating section 230 is an input section provided to the personal computer 201, such as a keyboard, a touch pad or a mouse, and is used for various input operations to perform a desired function in the information processing device 200.

The display section 240 has a display panel, and displays an icon and menu each having a predetermined function, and various information such as a connection state of the wrist device 100 and a transfer state of a target pace.

As with the wrist device 100, the memory section 260 broadly has a data storage memory (a data memory), a program storage memory (a program memory), a work data storage memory (a work memory), and a target pace database.

The data memory stores various data for use in various programs executed in the information processing device 200 and a target pace extracted from the target pace database.

The program memory stores control programs for achieving various functions in the information processing device 200 and an algorithm program for extracting a target pace from the target pace database based on training history of the user US and predetermined various conditions and transferring the target pace to the wrist device 100.

The work memory temporarily stores various data for use in executing each of the programs described above and various data generated.

The target pace database stores a target pace for using in performing the exercise support method as described in the first embodiment in the wrist device 100, or various data for generating a target pace.

The computation circuit 250 executes various control programs stored in the program memory, and thereby controls an operation at each component such as a display operation at the display section 240 and a data transfer operation at the communication function section 270.

The computation circuit 250 executes a predetermined algorithm program and thereby performs an operation of extracting, from the target pace database, a target pace to be set for each running section of the running course based on the training history and the predetermined various conditions, and transferring the target pace to the wrist device 100.

The communication function section 270 functions as an interface when a transfer request signal regarding a target pace is received from the wrist device 100 and when the target pace of each running section extracted from the target pace database is transferred to the wrist device 100.

Here, as a scheme of transmitting and receiving a transfer request signal and a target pace between the information processing device 200 and the wrist device 100 via the communication function section 270, a non-contact data transfer pad 202 can be applied, as depicted in FIG. 6B, for example. In this instance, by placing the wrist device 100 on the non-contact data transfer pad 202, it is possible to transmit and receive data as well as charge the operation power supply 190 simultaneously.

As another scheme, any of various wireless communication schemes may be applied. Alternatively, a wired communication scheme may be applied in which the information processing device 200 and the wrist device 100 are directly connected via a communication cable.

The clock circuit 280 generates an operation clock that regulates an operation timing of each component of the information processing device 200.

As the operation power supply 290, a secondary battery such as a lithium-ion battery or a commercial alternating current power supply is applied. The operation power supply 290 supplies driving electric power to each component of the information processing device 200.

In the exercise support device having the above-described configuration, firstly, when the user US is not using (wearing) the wrist device 100, the user US places the wrist device 100 on the data transfer pad 202, as depicted in FIG. 6B, or connects the wrist device 100 to the information processing device 200 by any of various wireless communication schemes or wired communication schemes, whereby the wrist device 100 is set in a state where the wrist device 100 can transmit and receive data to and from the information processing device 200.

Next, when the user US operates the input interface section 130 of the wrist device 100 to input various conditions of the running course, the computation circuit 150 of the wrist device 100 generates a transfer request signal for requesting transfer of a target pace to be set for each running section of the running course.

Then, when this transfer request signal is transmitted from the wrist device 100 to the information processing device 200, the computation circuit 250 of the information processing device 200 extracts a target pace for each running section from the target pace database of the memory section 260 based on the training history of the user US and predetermined various conditions, and transfers the target pace to the wrist device 100 via the communication function section 270.

The target pace transferred to the wrist device 100 is stored in a predetermined storage area of the data memory 161 of the memory section 160 in association with the each running section.

As another scheme of the target pace setting method, when the user US operates the input operating section 230 of the information processing device 200 to input an entire running distance of the running course, the computation circuit 250 extracts a target pace from the target pace database of the memory section 260 and transfer the target pace to the wrist device 100 via the communication function section 270, as with the above.

The target pace transferred to the wrist device 100 is stored in the data memory 161 in association with each running section.

As a result, the target pace is set for each running section.

Thereafter, as with the above-described embodiment, the series of operation processing at Step S102 onward of the exercise support method depicted in FIG. 3 is sequentially performed.

According to the present embodiment, it is not required to include a target pace database in the wrist device 100. Accordingly, the number of components and production cost of the wrist device 100 can be reduced.

Furthermore, when the user US is not using the wrist device 100, the target pace extracting operation can be performed by the external information processing device 200, and the target pace can be transferred to the wrist device 100 and set therein. As a result, processing load at the wrist device 100 can be reduced.

Still further, the user US can conduct running based on the target pace immediately upon wearing the wrist device 100.

In the present embodiment, the target pace database which stores target paces or various data for generating a target pace is incorporated in the memory section 260 of the information processing device 200. However, the present invention is not limited thereto. For example, as a so-called external hard disk, the target pace database is configured to be connected outside the information processing device 200.

Figure 8:
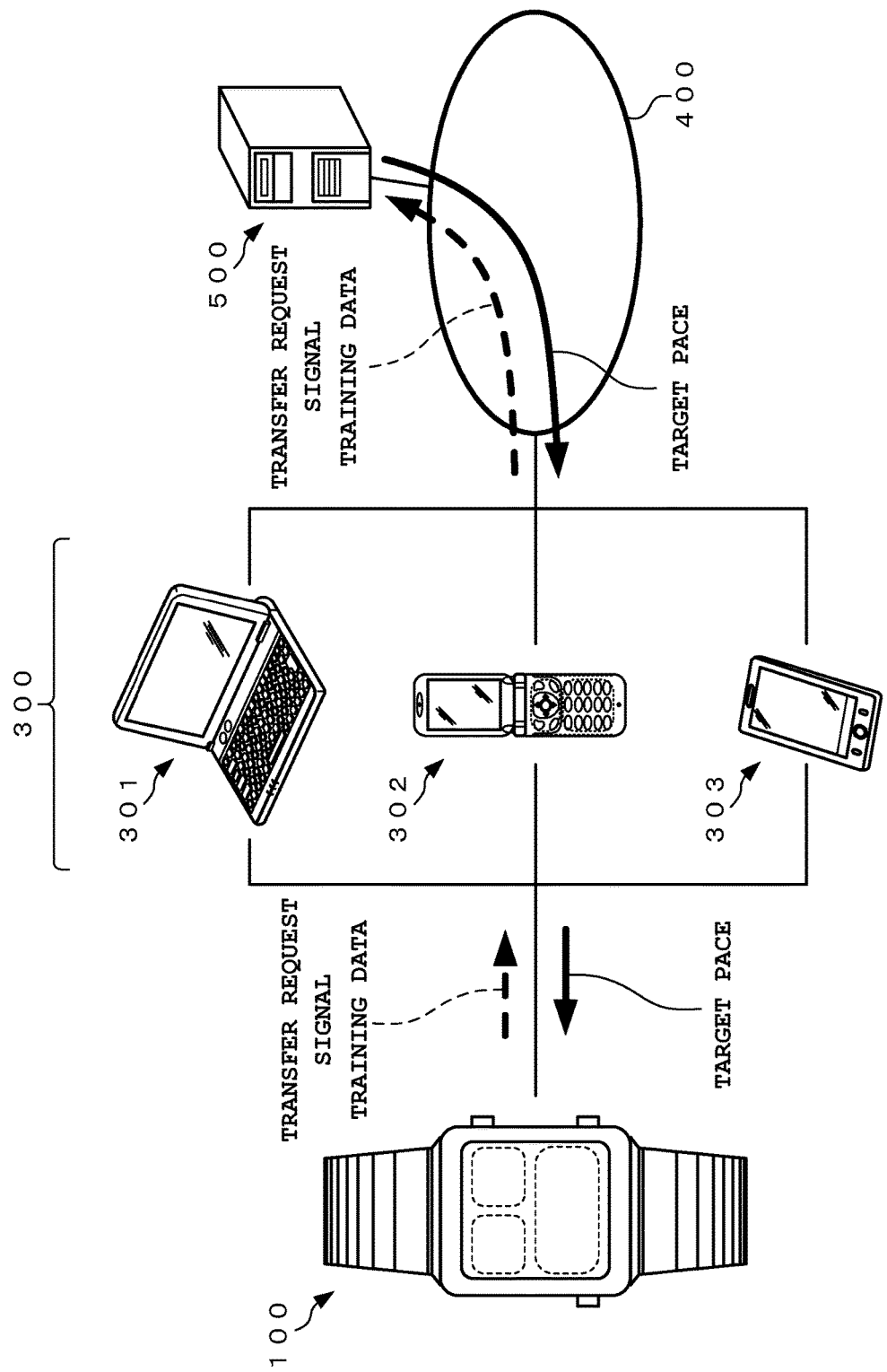
FIG. 8 is a schematic structural diagram of a second example of the second embodiment of the exercise support device according to the present invention.

FIG. 8 is a schematic structural diagram of a second example of the second embodiment of the exercise support device according to the present invention.

Figure 9:
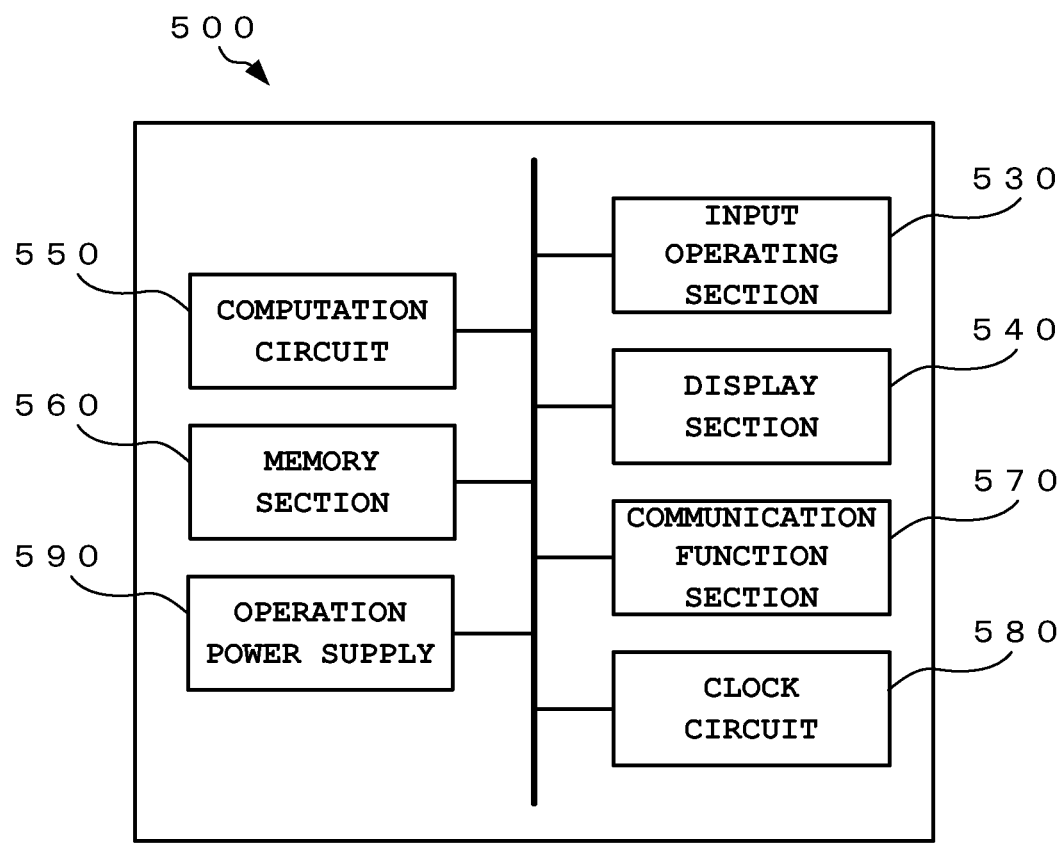
FIG. 9 is a block diagram of main sections depicting an example of control configuration of an information processing device applied to the exercise support device according to the second embodiment.

FIG. 9 is a block diagram of main sections depicting an example of control configuration of an information processing device applied to the exercise support device according to the present embodiment.

Here, components equivalent to those of the first embodiment are provided with the same reference numerals for simplification of description.

A second example of the exercise support device according to the second embodiment broadly has the wrist device 100, an information communication terminal 300, a network 400, and a network server 500, as depicted in FIG. 8, for example.

Here, the wrist device 100 has configuration in which the target pace database 164 is omitted (is not included) in the memory section 160, as with the described first example.

The information communication terminal 300 has configuration in which the target pace database in the memory section 260 is omitted (is not included) in the information processing device 200 described in the first example.

The information communication terminal 300 includes configuration equivalent to that of the information processing device 200 described in the first example. In addition, the communication function section 270 includes not only a function of transmitting and receiving data to and from the wrist device 100 but further includes a function of connecting to the network 400 such as the Internet.

As the above-described information communication terminal 300, a laptop-type or desktop-type personal computer 301 or a network communication device such as a portable telephone 302, a high-functionality portable telephone (hereinafter referred to as a "smartphone") 303, a tablet terminal or a dedicated terminal can be applied, as depicted in FIG. 8, for example.

In particular, the commercially-available network communication device such as the portable phone 302, the smartphone 303, or a tablet terminal has already included the function of connecting to the network 400. As a result, the network communication device can be easily connected to the network 400 regardless of location as long as the network communication device is within a prescribed communicable range.

In the present embodiment, by the information communication terminal 300, the wrist device 100 and the network server 500 connected to the network 400 are connected in a state where data is transmitted and received therebetween. Accordingly, it is possible to achieve at least functions of transmitting a transfer request signal from the wrist device 100 to the network server 500 and transferring a target pace for each running section from the network server 500 to the wrist device 100.

The network server 500 broadly includes configuration and functions equivalent to those of the information processing device 200 described in the first example.

Specifically, network server 500 broadly includes an input operating section 530, a display section 540, a computation circuit 550, a memory section 560, a communication function section 570, a clock circuit 580, and an operation power supply 590, as depicted in FIG. 9, for example.

Here, the input operating section 530, the display section 540, the clock circuit 580, and the operation power supply 590 have functions equivalent to the functions of the input operating section 230, the display section 240, the clock circuit 280, and the operation power supply 290 of the information processing device 200, respectively, and therefore are not described herein.

As with the information processing device 200, the memory section 560 broadly has a data memory, a program memory, a work memory, and a target pace database.

The program memory stores an algorithm program for extracting a target pace from the target pace database based on training history of the user US and predetermined various conditions and transferring the target pace to the wrist device 100.

The target pace database stores target paces for using in the exercise support method to be executed at the wrist device 100, or various data for generating a target pace.

The computation circuit 550 executes a predetermined algorithm program and thereby performs an operation of extracting, from the target pace database, a target pace to be set for each running section of the running course based on the training history and the predetermined various conditions, and transferring the target pace to the wrist device 100 via the network 400 and the information communication terminal 300.

The communication function section 570 functions as an interface when a transfer request signal regarding a target pace transmitted from the wrist device 100 is received via the information communication terminal 300 and the network 400 and when the target pace of each running section extracted from the target pace database is transferred to the wrist device 100 via the network 400 and the information communication terminal 300.

In the exercise support device having the above-described configuration, firstly, when the user US is not using (wearing) the wrist device 100, the user US connects the wrist device 100 to the information communication terminal 300 by any of various wireless communication schemes or wired communication schemes, whereby the wrist device 100 is set in a state where the wrist device 100 can transmit and receive data to and from the information communication terminal 300.

Next, the information communication terminal 300 is connected to the network 400 by any of various wireless communication schemes or wired communication schemes, whereby the information communication terminal 300 is set in a state where the information communication terminal 300 can transmit and receive data transmission and reception to and from the network server 500.

Next, when the user US operates the wrist device 100 or the information communication terminal 300 to input various conditions of the running course, a transfer request signal for requesting transfer of a target pace to be set for each running section of the running course is generated at the wrist device 100 or the information communication terminal 300.

Then, the generated transfer request signal is transmitted via the information communication terminal 300 and the network 400 to the network server 500.

The computation circuit 550 of the network server 500 extracts a target pace for each running section from the target pace database of the memory section 560 based on training history of the user US and predetermined various conditions, and transfers the target pace to the wrist device 100 via the network 400 and the information communication terminal 300.

As a result, in the wrist device 100, the target pace is set for each running section. Thereafter, as with the above-described embodiment, the series of operation processing at Step S102 onward of the exercise support method depicted in FIG. 3 is sequentially performed.

Also in the present embodiment, it is not required to include a target pace database in the wrist device 100. Accordingly, the number of components and production cost of the wrist device 100 can be reduced.

Furthermore, when the user US is not using the wrist device 100, the target pace extracting operation can be performed by the external network server 500, and the target pace can be transferred to the wrist device 100 and set therein. As a result, processing load at the wrist device 100 can be reduced. Still further, the user US can conduct running based on the target pace immediately upon wearing the wrist device 100.

In particular, in the present embodiment, the target pace extracting operation can be performed by using a large-capacity storage device provided to the network server 500 connected to the network 400. Accordingly, an optimum target pace can be extracted and set from an enormous amount of training data and can be used for pace making.

In the present embodiment, the target pace database is incorporated in the memory section 560 of the network server 500. However, the present invention is not limited thereto. For example, a storage section externally provided to the network server 500 may be applied as a target pace database.

Also in the first and second examples described in the present embodiment, as with the first embodiment described above, the GPS data obtained during running by the exercise support method and the geographic information, meteorological information, etc., of the running course may be stored in the target pace database of the information processing device 200 or the network server 500 as training data, and the database may be sequentially updated.

In each of the embodiments described above, running is exemplarily described as an exercise to which the exercise support device and exercise support method according to the present invention are applied. However, the present invention is not limited thereto.

For example, the exercise support device and exercise support method according to the present invention may be applied to various exercises such as walking, cycling, and wheel-chair racing.

Furthermore, in each of the embodiments described above, the virtual object 11 and the object 21 each have a shape like a human. However, the present invention is not limited thereto.

For example, as these objects, a user's favorite character such as an animal may be set. For example, when the exercise support device and exercise support method according to the present invention are applied to an exercise using a human-powered vehicle such as a bicycle or wheel chair, the objects may be set for each having a shape like such a vehicle.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

What is claimed is:

1. An exercise support device comprising:
a display device which has a display area in which a first object corresponding to a virtual mobile object and a second object corresponding to a user are displayed;
a sensor which obtains a movement speed of the user; and
a controller which controls a first display position of the first object and a second display position of the second object in the display area,
wherein the display area includes a first area and a second area which are different from each other, and
wherein the controller performs control such that:
in a case in which the user moves in a section from a first point to a second point on a course set in advance, a starting point position corresponding to the first point and an ending point position corresponding to the second point are set in the display area; and
while the user is moving in the section from the first point to the second point, (i) the first display position of the first object is moved between the starting point position and the ending point position, so as to correspond to a first movement distance that is calculated based on a set target pace and an elapsed time after the user starts movement in the section, (ii) the second display position of the second object is moved between the starting point position and the ending point position, so as to correspond to a second movement distance that the user has actually moved in the section in the elapsed time, (iii) in a case in which the first display position of the first object is between the starting point position and the ending point position, a value of the target pace is displayed in the first area simultaneously with the first object, and a value of a running pace based on the movement speed of the user is displayed in the second area simultaneously with the second object, and (iv) when the first object has reached the ending point position before the user reaches the second point, a value of the running pace of the user at a time at which the first object has reached the ending point position is displayed in the first area.

2. The exercise support device according to claim 1, wherein the starting point position and the ending point position are two positions which are arranged separately from each other along a first direction on the display area, and
wherein the controller performs control such that, at a time at which the user starts moving in the section, the first display position of the first object and the second display position of the second object are respectively set at two start positions which are positions that coincide with the starting point position in the first direction and which are arranged separately from each other along a second direction orthogonal to the first direction.

3. The exercise support device according to claim 2, wherein the controller, while the user is moving in the section, performs control such that:
the first movement distance is calculated as a value which is a product of the target pace multiplied by the elapsed time,
the first display position of the first object moves along the first direction between the starting point position and the ending point position according to a change of the first movement distance in the elapsed time at each constant time interval, the second display position of the second object moves along the first direction between the starting point position and the ending point position according to a change of the second movement distance in the elapsed time at the each constant time interval, and a bar graph indicating a position of the user in the section at the each constant time interval is displayed in the display area according to a change of the second movement distance in the elapsed time at the each constant time interval.

4. The exercise support device according to claim 3, wherein the controller, when the first object has reached the ending point position before the user reaches the second point, performs control such that the first object is continuously displayed in a state in which the first object is kept at the ending point position, until the user reaches the second point.

5. The exercise support device according to claim 2, further comprising:
a storage section which accumulates therein information for generating the target pace;
an input operating section which provides an input of a scheduled movement route of the user; and
a target pace setting section which divides the scheduled movement route into a plurality of movement sections each having a predetermined distance, with a start point and an end point of each of the plurality of movement sections corresponding to the first point and the second point, respectively, and sets the target pace for each of the movement sections based on the information accumulated in the storage section.

6. The exercise support device according to claim 5, further comprising:
a movement speed obtaining section which obtains sensor data from the sensor associated with the movement speed of the user,
wherein the storage section accumulates past sensor data of the user obtained by the movement speed obtaining section as the information, and
wherein the target pace setting section sets the target pace based on the past sensor data of the user obtained by the movement speed obtaining section and accumulated in the storage section.

7. The exercise support device according to claim 6, wherein the target pace set by the target pace setting section is updated every time new sensor data of the user obtained by the movement speed obtaining section is accumulated in the storage section.

8. The exercise support device according to claim 6, wherein the input operating section, the movement speed obtaining section, the display device, and the controller are provided in a single device, and the single device is mounted on a body of the user while the user is moving.

9. The exercise support device according to claim 8, wherein the storage section and the target pace setting section are external information processing devices communicably connected to the device.

10. The exercise support device according to claim 9, wherein the information processing device is communicably connected to the device via a network.

11. The exercise support device according to claim 5, wherein the controller performs control such that, at a time at which the user moves to the end point of a first movement section other than a last movement section, from among the plurality of movement sections, and starts moving in a second movement section subsequent to the first movement section, the first display position of the first object and the second display position of the second object are each set to the starting point position.

12. The exercise support device according to claim 11, wherein the controller performs control such that:
the value of the target pace is displayed in the first area in a first display format,
the value of the running pace of the user is displayed in the second area in a second first display format which is different from the first display format, and
the value of the target pace, every time the movement section is changed, is updated to a value set for the movement section after being changed.

13. The exercise support device according to claim 1, wherein the first object and the second object are animation images which respectively have a human-like shape and are animated to move as if at least leg portions thereof perform a running motion.

14. An exercise support method comprising:
displaying a first object corresponding to a virtual mobile object and a second object corresponding to a user in a display area of a display device;
controlling, in a case in which the user moves in a section from a first point to a second point on a course set in advance, such that a starting point position corresponding to the first point and an ending point position corresponding to the second point are set in the display area, the display area including a first area and a second area which are different from each other;
controlling, while the user is moving in the section from the first point to the second point, such that (i) a first display position of the first object in the display area is moved between the starting point position and the ending point position, so as to correspond to a first movement distance that is calculated based on a set target pace and an elapsed time after the user starts movement in the section, and (ii) a second display position of the second object in the display area is moved between the starting point position and the ending point position, so as to correspond to a second movement distance that the user has actually moved in the section in the elapsed time;
controlling, in a case in which the first display position of the first object is between the starting point position and the ending point position, such that a value of the target pace is displayed in the first area simultaneously with the first object, and a value of a running pace based on a movement speed of the user is displayed in the second area simultaneously with the second object; and
controlling, when the first object has reached the ending point position before the user reaches the second point, such that a value of the running pace of the user at a time at which the first object has reached the ending point position is displayed in the first area.

15. The exercise support method according to claim 14, wherein the starting point position and the ending point position are two positions which are arranged separately from each other along a first direction on the display area, and
wherein, at a time at which the user starts moving in the section, the first display position of the first object and the second display position of the second object are respectively set as two start positions which are positions that coincide with the starting point position in the first direction and which are arranged separately from each other along a second direction orthogonal to the first direction.

16. The exercise support method according to claim 15, wherein, while the user is moving in the section, the first movement distance is calculated as a value which is a product of the target pace multiplied by the elapsed time, and the first display position of the first object moves along the first direction between the starting point position and the ending point position according to a change of the first movement distance in the elapsed time at each constant time interval, wherein, while the user is moving in the section, the second display position of the second object moves along the first direction between the starting point position and the ending point position according to a change of the second movement distance in the elapsed time at the each constant time interval, and wherein a bar graph indicating a position of the user in the section at the each constant time interval is displayed in the display area according to a change of the second movement distance in the elapsed time at the each constant time interval.

17. The exercise support method according to claim 16, wherein, when the first object has reached the ending point position before the user reaches the second point, the first object is continuously displayed in a state in which the first object is kept at the ending point position until the user reaches the second point.

18. The exercise support method according to claim 14, wherein the first object and the second object are animation images which respectively have a human-like shape and are animated to move as if at least leg portions thereof perform a running motion.

19. A non-transitory computer-readable storage medium having stored thereon a program that is executable by a computer, the program being executable by the computer to perform functions comprising:

processing for displaying a first object corresponding to a virtual mobile object and a second object corresponding to a user in a display area of a display device;

processing for controlling, in a case in which the user moves in a section from a first point to a second point on a course set in advance, such that a starting point position corresponding to the first point and an ending point position corresponding to the second point are set in the display area at two positions which are arranged separately from each other along a first direction of the display area, the display area including a first area and a second area which are different from each other;

processing for controlling, while the user is moving in the section from the first point to the second point, such that (i) a first display position of the first object in the display area is moved between the starting point position and the ending point position, so as to correspond to a first movement distance that is calculated based on a set target pace and an elapsed time after the user starts movement in the section, and (ii) a second display position of the second object in the display area is moved between the starting point position and the ending point position, so as to correspond to a second movement distance that the user has actually moved in the section in the elapsed time;

processing for controlling, in a case in which the first display position of the first object is between the starting point position and the ending point position, such that a value of the target pace is displayed in the first area simultaneously with the first object, and a value of a running pace based on a movement speed of the user is displayed in the second area simultaneously with the second object; and processing for controlling, when the first object has reached the ending point position before the user reaches the second point, such that a value of the running pace of the user at a time at which the first object has reached the ending point position is displayed in the first area.

* * * * *